United States Patent [19]

Daum et al.

[11] 3,972,930

[45] Aug. 3, 1976

[54] AMINOCYCLITOL ANTIBIOTICS

[75] Inventors: Sol J. Daum, Albany; Robert L. Clarke, Bethlehem, both of N.Y.

[73] Assignee: Sterling Drug Inc., New York, N.Y.

[22] Filed: Feb. 18, 1975

[21] Appl. No.: 550,273

[52] U.S. Cl. .................... 260/563 R; 260/563 C; 260/563 P; 195/96; 536/17
[51] Int. Cl.² ......................................... C07C 87/38
[58] Field of Search......... 260/563 R, 563 C, 563 P, 260/583 R, 583 C, 583 P

[56] References Cited
UNITED STATES PATENTS
3,112,345    11/1963    Stanbury ..................... 260/563 C

OTHER PUBLICATIONS

Peck et al., J. Am. Chem. Soc. 68, (1946), pp. 776–781.

Shier et al., J. Antibiotics, vol. 26, (1973), pp. 551–561.

*Primary Examiner*—Arthur P. Demers
*Attorney, Agent, or Firm*—William G. Webb; B. W. Wyatt

[57] ABSTRACT

Aminocyclitol analogs of gentamicin $C_1$, $C_2$ and $C_{1a}$ and the corresponding compounds acylated on the 1-, 3- and 2'-amino groups with an $\omega$-amino-$\alpha$-hydroxy-lower-alkanoyl group are prepared by culturing a nutrient medium containing carbohydrates, a source of assimilable nitrogen, essential salts and an added aminocyclitol with a mutant of *Micromonospora purpurea* and acylating the product with an ester of an $\omega$-(N-benzyloxycarbonyl)amino-$\alpha$-hydroxy-lower-alkanoic acid followed by catalytic hydrogenolysis of the benzyloxycarbonyl group.

1 Claim, No Drawings

AMINOCYCLITOL ANTIBIOTICS

BACKGROUND OF THE INVENTION a. Field of the Invention

This invention relates to aminocyclitol antibiotics of the gentamicin type useful as antibacterial agents.

b. Description of the Prior Art

The gentamicin complex of antibiotics produced by *Micromonospora purpurea* is known to consist primarily of three components designated $C_1$, $C_2$ and $C_{1a}$ having the structures:

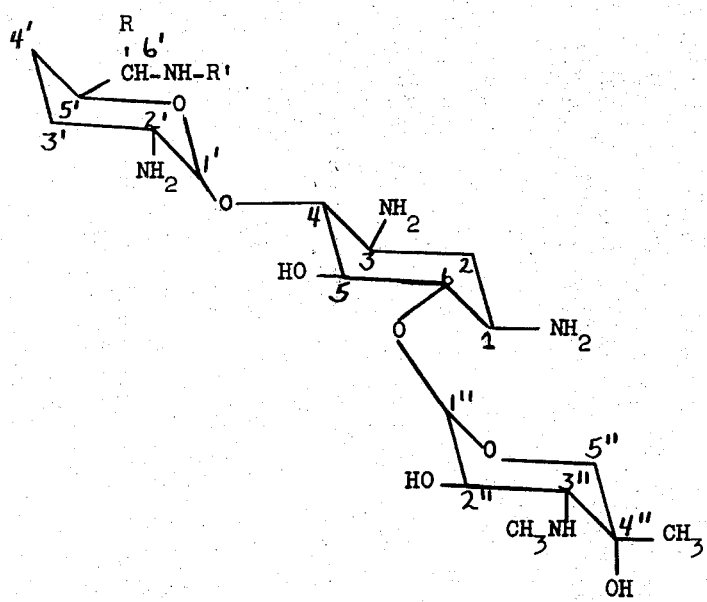

Gentamicin $C_1$: R = R' = $CH_3$

Gentamicin $C_2$: R = $CH_3$, R' = H

Gentamicin $C_{1a}$: R = R' = H (Cooper et al., J. Chem. Soc., Sect. C, 1971, 2876-2879; Konishi et al. U.S. Pat. No. 3,780,018, patented Dec. 18, 1973; British Patent No. 1,364,521, published Aug. 21, 1974; and Merck Index, Eighth Edition, page 485), and the 1-, 3- and 2'-(γ-amino-α-hydroxybutyryl) analogs of gentamicin $C_1$ are also known (Konishi et al., loc. cit.).

Moreover, it is known that certain aminocyclitol-type antibiotics can be prepared by culturing microrganism mutants in a medium containing carbohydrates, a source of assimilable nitrogen, essential salts and an aminocyclitol subunit, which is incorporated by the organism into the antibiotic (Shier et al., U.S. Pat. No. 3,669,838, patented June 13, 1972). In the case of the gentamicin complex of compounds, which are each derivatives of deoxystreptamine, the added aminocyclitol subunit in the Shier et al. process is deoxystreptamine.

SUMMARY OF THE INVENTION

In one of its composition of matter aspects, the present invention relates to certain aminocyclitol analogs of gentamicin $C_1$, $C_2$ and $C_{1a}$ which are described chemically as O-3-deoxy-4-C-methyl-3-methylamino-β-L-arabinopyranosyl-(1 → 6)-O-[2-amino-6-amino-(and 6-C-methyl and 6-methylamino-6-C-methyl)-2,3,4,6-tetradeoxy-α-D-erythro-glucopyranosyl-(1 → 4)]-streptamines. The invention also relates to the corresponding compounds acylated at one of the 1-, 3- and 2'-amino groups with a γ-amino-α-hydroxybutyryl or β-amino-α-hydroxypropionyl group.

In a second composition of matter aspect, the invention relates to certain novel streptamines which are useful as intermediates in the preparation of the O-3-deoxy-4-C-methyl-3-methylamino-β-L-arabinopyranosyl-(1 → 6)-O-[2-amino-6-amino (and 6-C-methyl and 6-methylamino-6-C-methyl)-2,3,4,6-tetradeoxy-α-D-erythro-glucopyranosyl-(1 → 4)]streptamine final products.

In one of its process aspects, the invention relates to a process for preparing the O-3deoxy-4-C-methyl-3-methylamino-β-L-arabinopyranosyl-(1 → 6)-O-[2-amino-6-amino- (and 6-C-methyl and 6-methylamino-6-C-methyl)-2,3,4,6-tetradeoxy-α-D-erythro-glucopyranosyl-(1 → 4)]streptamine final products comprising culturing a nutrient medium containing carbohydrates, a source of assimilable nitrogen, essential salts and an added aminocyclitol with a mutant of *Micromonospora purpurea*.

In a second process aspect, the invention relates to a process for preparing O-3-deoxy-4-C-methyl-3-methylamino-β-L-arabinopyranosyl-(1 → 6)-O-[2-amino-6-amino- (and 6-C-methyl-and 6-methylamino-6-C-methyl)-2,3,4,6-tetradeoxy-α-D-erythro-glucopyranosyl-(1 → 4)]streptamines acylated on one of the 1-,3- or 2'-amino groups with an ω-amino-α-hydroxy-lower-alkanoyl group comprising reacting an O-3-deoxy-4-C-methyl-3-methylamino-β-L-arabinopyranosyl-(1 → 6)-O-[2-amino-6-amino-(and 6-C-methyl and 6-methylamino-6-C-methyl)-2,3,4,6-tetradeoxy-α-D-erythro-glucopyranosyl-(1 → 4)]streptamine with an N-hydroxysuccinimide ester of an ω-(N-benzyloxycarbonyl)amino-α-hydroxy-lower-alkanoic acid and hydrogenolysis of the benzyl-oxycarbonyl group in the resulting product with hydrogen over a catalyst.

DETAILED DESCRIPTION INCLUSIVE OF THE PREFERRED EMBODIMENTS

More specifically, this invention relates to compounds having the formula:

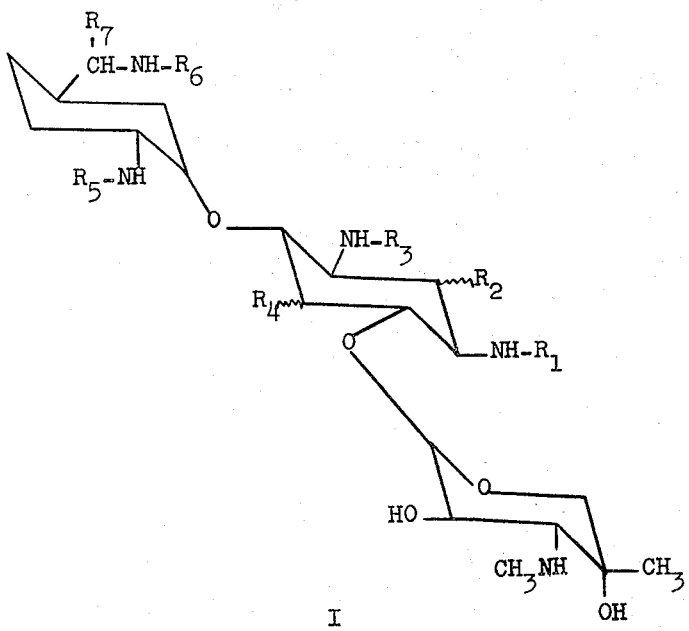

I where $R_1$, $R_3$ and $R_5$ represent hydrogen, or one of them represents an ω-amino-α-hydroxy-lower-alkanoyl group having the formula:

$H_2NCH_2(CH_2)_nCHOHCO-$ where $n$ is zero or 1, the other of $R_1$, $R_3$ and $R_5$ being hydrogen; $R_2$ represents hydrogen or hydroxy; $R_4$ represents hydrogen, hydroxy or halogen (including fluorine, chlorine, bromine and iodine), except that when $R_2$ is hydrogen, $R_4$ is not hydroxy cis to the amino groups at the 1- and 3-positions; and $R_6$ and $R_7$ each represent hydrogen or methyl.

The compounds of formula I where $R_1$, $R_3$ and $R_5$ are hydrogen are prepared by the method described in Shier et al. U.S. Pat. No. 3,669,838. This method comprises culturing a nutrient medium containing carbohydrates, a source of assimilable nitrogen, essential salts and an added aminocyclitol derivative having the formula:

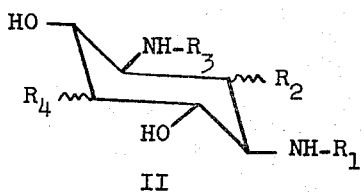

II where $R_1$, $R_2$, $R_3$ and $R_4$ have the meanings given above, and where $R_1$ and $R_3$ can in addition represent a single bond joining the two amino nitrogen atoms together, and a mutant of *Micromonospora purpurea*, designated *Micromonospora purpurea* ATCC 31,119, and isolating the product from the culture medium. The compounds of formula I where both $R_1$ and $R_3$ are hydrogen are produced when the aminocyclitol of formula II and where $R_1$ and $R_3$ represent a single bond is used. In accordance with the procedure described by Shier et al., the nature of the mutant is such that it is incapable of synthesizing the aminocyclitol subunit from a nutrient medium to thereby produce the antibiotic, but is capable of incorporating the latter into an antibiotic when the aminocyclitol is added to the nutrient medium.

The compounds of formula I, where one of $R_1$, $R_3$ and $R_5$ represents an ω-amino-α-hydroxy-lower-alkanoyl group, are prepared by the method described by Konishi et al., U.S. Pat. No. 3,780,018 which comprises reacting the compound of formula I where each of $R_1$, $R_3$ and $R_5$ is hydrogen with an N-hydroxysuccinimide ester having the formula:

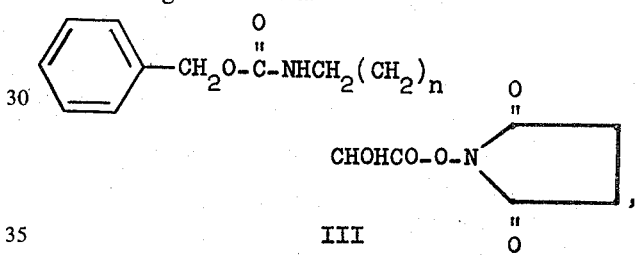

III where $n$ has the meanings given above. The resulting mixture of the compounds of formula I where one of $R_1$, $R_3$ and $R_5$ is the ω-(N-benzyloxycarbonyl)amino-α-hydroxy-lower-alkanoyl group:

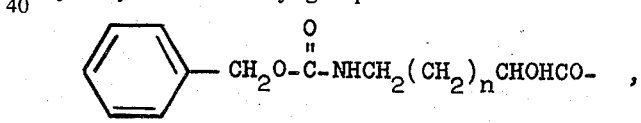

the other two being hydrogen, is then subjected to hydrogenolysis of the benzyloxycarbonyl group with hydrogen over a catalyst.

As indicated above, when a compound of formula I where each of $R_1$, $R_3$ and $R_5$ is hydrogen is used as starting material in the acylation reaction, a mixture of the three possible isomeric mono-amides is obtained in which one of the $R_1$, $R_3$ or $R_5$ amine hydrogen atoms is replaced by the ω-(N-benzyloxycarbonyl)amino-α-hydroxy-lower-alkanoyl group. When individual characterization and study of these products are desired, they must of course be separated from one another. The acylation reaction is carried out by reacting molar equivalent amounts of the compound of formula I and the N-hydroxysuccinimide ester, preferably at a temperature from −10°C. to about 10°C., and in an aqueous solution of an inert organic solvent, for example tetrahydrofuran, dioxane, ethyleneglycol dimethyl ether, dimethylacetamide, dimethylformamide, propyleneglycol dimethyl ether, and the like.

Hydrogenolysis of the benzyloxycarbonyl group is carried out over a palladium-on-charcoal catalyst in an inert, water miscible organic solvent, for example methanol, ethanol, dioxane, tetrahydrofuran, ethyleneglycol dimethyl ether, propyleneglycol dimethyl ether, and the like.

The aminocyclitols of formula II where $R_1$, $R_2$ and $R_3$ are hydrogen and $R_4$ is fluorine or iodine are novel compounds, which are considered to be within the purview of the instant invention, and are prepared as described hereinbelow. Other aminocyclitols of formula II, which are also useful in the practice of the present invention, are known compounds. These are:

streptamine sulfate [Peck et al., J. Am. Chem. Soc. 68, 776 (1946)];

2-epistreptamine dihydrochloride [Suami et al., J. Org. Chem. 33, 2831 (1968)];

2,5-dideoxystreptamine dihydrochloride, m.p. >300°C.;

6,7-diazabicyclo[3.2.1]octane-2,4-diol (exo, exo), m.p. 185–193°C. [Both the latter two compounds disclosed by Testa et al., J. Antibiotics 27, 917–921 (1974)].

The N-hydroxysuccinimide esters of formula III are a generally known class of compounds.

The compounds of formula I have been tested in a standard serial dilution antibacterial test and have been found to have antibacterial activity, particularly against gentamicin resistant organisms. The compounds are thus useful as anti-bacterial agents.

The compounds of formula I are primarily intended for oral, topical or parenteral administration and can be prepared for use by suspension, either in the form of their free bases or as pharmaceutically acceptable, non-toxic acid addition salts, in an inert carrier such as polyethylene glycol, or by tabletting or encapsulation for oral administration either alone or with suitable adjuvants, or alternatively they can be formulated with conventional creams or jellies for topical application.

The molecular structures of the compounds of the invention were assigned on the basis of their method of preparation, and study of their chromatographic characteristics and their nuclear magnetic resonance (nmr) and mass spectra and were confirmed by the correspondence betweeen calculated and found values for elementary analyses for the elements.

The following specific examples are illustrative of the manner of making the compounds of the invention without being limited thereto.

Preparation of Novel Streptamines Preparation 1

2-Deoxy-1,6:3,4-dicarbonylstreptamine [Umezawa et al. Bull. Chem. Soc. (Jap.) 44, 1411–1415 (1971)] (47 g., 0.21 mole) was suspended in 500 ml. of pyridine and the stirred suspension treated with 45 ml. of methanesulfonyl chloride. After cooling, the mixture was diluted with about 3 liters of methanol and the product filtered and dried to give 39 g. of 2-deoxy-5-methanesulfonyl-1,6:3,4-dicarbonylstreptamine, m.p. 264–266°C.

A mixture of 2g. (0.0069 mole) of 2-deoxy-5-methanesulfonyl-1,6:3,4-dicarbonylstreptamine, described above, and 4.8 g. (0.032 mole) of sodium iodide in 70 ml. of dimethylformamide was heated at 125°C. for 24 hours and then taken to dryness. The crude 2,5-dideoxy-5-iodo-1,6:3,4-dicarbonylstreptamine was mixed with 30 ml. of 6N hydrochloric acid, the mixture refluxed for 2½ hours and then cooled and evaporated to dryness in vacuo. The crude 2,5-dideoxy-5-iodostreptamine dihydrochloride was dissolved in 30 ml. of acetic anhydride, the solution treated with 5.25 g. of sodium acetate and the mixture refluxed for two and a half hours. The mixture was then cooled, poured into 200 ml. of water and extracted with chloroform. The chloroform extracts, on washing once with sodium thiosulfate solution, once with brine, once with water and evaporation to dryness, afforded an oil which was crystallized from ethanol to give two crops totaling 1.1 g. of N,N'-diacetyl-2,5-dideoxy-5-iodostreptamine, m.p. 256°–258°C. Hydrolysis of the latter by refluxing with aqueous hydrochloric acid and isolation from a basic medium affords 2,5-dideoxy-5-iodostreptamine.

Preparation 2

2-Deoxy-5-methanesulfonyl-1,6:3,4-dicarbonylstreptamine (39 g., 0.12 mole), described in Preparation 1 above, was suspended in approximately 200 ml. of 6N hydrochloric acid, the mixture warmed on a steam bath for two hours, evaporated to dryness in vacuo, mixed with 200 ml. of isopropyl alcohol and evaporated to dryness once again. The residual oil was triturated with methanol, cooled and the solid collected and recrystallized from methanol to give 2-deoxy-5-methanesulfonylstreptamine dihydrochloride, m.p. 208°–210°C.

Anal. Calcd. for $C_7H_{16}N_2O_5S \cdot 2HCl$: C,26.84; H,5.79; N,8.94. Found: C,26.77; H, 5.76; N,9.17.

A solution of 28.7 g. (0.09 mole) of 2-deoxy-5-methanesulfonylstreptamine in 45 ml. of water and 90 ml. of 2N sodium hydroxide was cooled in an ice bath and treated dropwise with stirring with a solution of 45 ml. of benzyl chloroformate in 80 ml. of toluene added from one dropping funnel and with 160 ml. of 2N sodium hydroxide from another. When addition was complete, the mixture was stirred for an additional 15 minutes, diluted with about 50 ml. of toluene, stirred for 3 hours and filtered. Recrystallization of the solid from ethanol afforded 4.0 g. of N,N'-dicarbobenzoxy-2-deoxy-5-methanesulfonylstreptamine, m.p. 198°–201°C.

Anal. Calcd. for $C_{23}H_{28}N_2O_9S$: C,54.32; H,5.55; N,5.51. Found: C,54.75; H,5.61; N,5.60.

Reaction of the latter with potassium fluoride in benzene or acetonitrile containing a crown ether, e.g. 1,4,7,10,13,16-hexaoxacyclooctadecane, using the procedure described by Liotta et al., J. Am. Chem. Soc. 96, 2250–2252 (1974) affords N,N'-dicarbobenzoxy-2,5-dideoxy-5-fluorostreptamine which, on hydrolysis with aqueous mineral acid, affords 2,5-dideoxy-5-fluorostreptamine.

Mutation Process

In the following procedures various media constituted as follows were employed.

| Medium 1: | N-Z Amine | g./l. |
|---|---|---|
| | Glucose | 10g. |
| | Soluble starch | 20g. |
| | Yeast extract | 5g. |
| | N-Z-Amine-Type A (Difco) | 5g. |
| | $CaCO_3$ | 1g. |
| | Agar | 15g. |
| Medium 2: | Germination Medium (in distilled water) | |
| | Beef extract | 0.3% |
| | Tryptone | 0.5% |
| | Dextrose | 0.1% |
| | Soluble starch | 2.4% |
| | Yeast extract | 0.5% |
| | $CaCO_3$ | 0.4% |
| Medium 3: | Soybean-Glucose | g./l. |
| | Soybean meal | 30g. |
| | Dextrose (cerelose) | 40g. |
| | $CaCO_3$ | 1g. |
| Medium 4: | TGE | |

| -continued | |
|---|---|
| | g./l. |
| Trypticase glucose extract | 5.0g. |
| Trypticase peptone | 3.0g. |
| Glucose | 1.0g. |
| Agar | 15.0g. |

The organism *Micromonospora purpurea* was obtained from the U.S. Dept. of Agriculture as NRRL 2953 and maintained on N-Z amine slants (medium 1). Submerged fermentations were conducted in flasks containing germination medium 2 for 4 days at 37°C. on a rotary shaker. From this first stage seed, a 10% inoculum was transferred to the germination medium (Medium 2), and fermentation was continued as above at 28°C. for 7 days.

For purposes of establishing the capability of the organism to biosynthesize gentamicin in the absence of added deoxystreptamine, a third stage fermentation using a 5% inoculum was carried out in a 10 liter fermentor in a soybean-glucose medium (3) at 28°C., agitating at 200 rpm and sparging at 2 liters/minute with filtered air. After 6 days, the tank contents were acidified to pH 2.0 with 6N sulfuric acid, filtered, and a 500 ml. portion neutralized with ammonium hydroxide and passed through an IRC-50 ion exchange resin ($Na^+$ form). The column was then rinsed with water and eluted with 2N sulfuric acid. Following the procedure described in U.S. Pat. No. 3,091,572, there was isolated a 300 mg. sample of crude gentamicin, which was found to be biologically active and which contained three components similar to gentamicin $C_1$, $C_2$ and $C_{1a}$ by TLC examination.

For purposes of mutating the organism broth cultures were cultivated in medium 2 (37°C. for 3 days) and the resultant cells harvested by centrifugation, washed and resuspended in buffered saline. This suspension was treated with the mutagenic agent, N-methyl-N'-nitro-N-nitrosoguanidine. Samples of the mutagenized culture were plated in medium 4 at 37°C. until colonies were evident (usually about one week). Colonies were picked to duplicate plates (medium 4), one set of which was overlaid with a spore suspension of *B. subtilis*. After incubation at 37°C. for from 18 to 20 hours, the "picks" which showed no zone of inhibition on the *B. subtilis* plate were transferred from the master plate (no *B. subtilis*) to medium 1 slants and incubated until full growth was evident.

These potential nonproducing mutants were then challenged with deoxystreptamine in an attempt to stimulate antibiotic biosynthesis as follows. Stock cultures of the potential mutants were streaked as bands on the surface of medium 4 plates and incubated at 37°C. until growth was evident (about 3 to 4 days). Filter paper discs were then dipped into a solution of deoxystreptamine (500 mcg./ml.) and placed on top of the culture streak. After incubation for 24 hours, the surface of the plate was inoculated with *B. subtilis* using the overlay technique, and incubation was continued for an additional eighteen to twenty hours. Isolates showing zones of inhibition surrounding the disc were designated as deoxystreptamine mutants. One such mutant, coded mutant VIB and deposited with the American Type Culture Collection, 12301 Parklawn Drive, Rockville, Md. 20852 as *Micromonospora purpurea* ATCC 31,119, was used for the production of the gentamicin-type antibiotics as described below.

Biosynthesis of Antibiotics with Mutant VIB

EXAMPLE 1

The mutant organism was maintained on N-Z amine agar slants (medium 1) from which transfers to flasks containing 500 ml. of germination medium 2 were made. The flasks were incubated at 28°C. for 4 days on a rotary shaker (2 inch stroke) at 225 rpm.

A 10% (v/v) inoculum from the germination stage was aseptically transferred to 14 liter fermentors containing 9 liters of sterile germination medium 2. These were agitated at 450 rpm at 28°–29°C. and sparged with filtered air at 5 liters/minute. At time of inoculation, 200 mg./liter of streptamine sulfate was added as a suspension in sterile distilled water. Fermentation was continued for 8 days.

A twenty-four hour, 10 liter inoculum prepared as above was aseptically transferred to 130 liter fermentors containing 70 liters of sterile germination medium 2, and 0.31 g./liter of streptamine sulfate suspended in sterile distilled water was added. Aerobic fermentation was carried out at 29°C. for 7 days.

Fermentations were terminated by addition of 10N sulfuric acid to pH 2.0 and filtration using a filter aid to remove mycelia. The filtered broth was adjusted to pH 7.0, and 1.56 g. of oxalic acid per gram of calcium carbonate present in the medium was added t remove calcium. This was allowed to stand overnight, and the clarified broth was decanted and passed over Bio-Rex 70 (weak cation exchanger) resin in the $Na^+$ form using about 14 g. of resin per liter of broth. The column was then washed with distilled water and eluted with 2N sulfuric acid. All fractions displaying antibiotic activity were combined, neutralized and concentrated under vacuum below 50°C. to the point where salt crystallization became evident (about ⅓ volume). The pH was then adjusted to 10.5, and four volumes of acetone were added to precipitate inorganics which were removed by filtration. The filtrate was adjusted to pH 5.0 with 6N sulfuric acid, concentrated under vacuum to approximately 1/20 of the original volume and chilled. A white crystalline crop melting over 300°C. was collected by filtration which was found, from its thin layer chromatography properties and its infrared spectrum, to be identical to streptamine sulfate. From two 10 liter fermentations processed as above, a total of 0.7 g. of streptamine sulfate was obtained, and from two 80 liter fermentations, a total of 21 g. of streptamine sulfate was recovered at this step.

The filtrate was further concentrated and 10 volumes of methanol added yielding the first crude antibiotic solid. From two 10 liter fermentations, 7 g. was obtained, and from two 80 liter fermentations, 24 g. was obtained.

For purpses of identifying antibiotic components during purification procedures, chromatographic mobility values obtained on paper chromatography and thin layer chromatography were determined for gentamicins $C_1$, $C_2$ and $C_{1a}$ and for each of the corresponding aminocyclitol analogs prepared as indicated above, where the chromatographic mobility (hereinafter designated C.M.) is expressed as:

$$C.M. = \frac{\text{distance component from origin}}{\text{distance gentamicin } C_1 \text{ from origin}}.$$

The chromatography systems used were as follows:

System 1

Whatman No. 1 paper saturated with 0.95M sulfate-bisulfate and developed in descending fashion in 80% aqueous ethanol + 1.5% NaCl and subsequent bioautography using B. subtilis as test organism.

System 2 - Silica gel F 254 plate developed in lower phase of chloroform(1):methanol(1):concentrated(28%)ammonium hydroxide(1). Components were located with a ninhydrin spray on heating.

The C.M. Values of the major antibiotic components of the present invention in comparison with a reference gentamicin complex, all relative to gentamicin $C_1$, are shown in Table I, where the compounds designated Component 1, Component 2 and Component 3 are to be understood to be, respectively, O-3-deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-D-streptamine;

O-3-deoxy-4-C-methyl-3-methylamino-$\beta$-L-arabinopyranosyl-(1 → 6)-O-[2,6-diamino-6-C-methyl-2,3,4,6-tetradeoxy-$\alpha$-D-erythro-glucopyranosyl-(1 → 4)]-D-streptamine; and O-3-deoxy-4-C-methyl-3-methylamino-$\beta$-L-arabinopyranosyl-(1 → 6)-O-[2,6-diamino-2,3,4,6-tetradeoxy-$\alpha$-D-erythro-glucopyranosyl-(1 → 4)]-D-streptamine.

Table I

|  | C.M. System 1 | C.M. System 2 |
| --- | --- | --- |
| Gentamicin $C_1$ | 1 | 1 |
| Gentamicin $C_2$ | 0.89 | 0.83 |
| Gentamicin $C_{1a}$ | 0.50 | 0.67 |
| Component 1 (Major) | 0.96 | 0.92 |
| Component 2 (Minor) | 0.76 | 0.75 |
| Component 3 (Minor) | 0.50 | 0.61 |

From the 10 liter fermentors, the crude solid (7 g.), which displayed antibacterial activity, was suspended in 200 ml. of methanol and 10 ml. of concentrated (28%) ammonium hydroxide, and the mixture agitated for thirty minutes and filtered. This was repeatd two additional times, and the filtrates were combined and concentrated under vacuum yielding a pale yellow oil weighing 0.9 g. The "spent salts" were essentially devoid of antibiotic activity.

The oily base was mixed with 4 g. of silica gel (Davison grade 923, 100–200 mesh) and charged on a silica gel column measuring 1.8 × 28 cm. The column was prepared as a slurry using the lower phase of isopropyl alcohol(1):chloroform (2):17% aqueous ammonium hydroxide(1). The column was developed with this solvent and 50 ml. fractions collected.

Fractions 8 and 9 contained a single ninydrin-positive component which yielded 20 mg. as a pale yellow oil on removal of solvent. The mass spectrum of this material, designated Component 1, showed a molecular ion and major fragments each 16 mass units (i.e. one oxygen atom) greater than that obtained from gentamicin $C_1$ as follows:

Reference gentamicin $C_1$: $M^+$ 477, 420, 360, 350, 347, 322, 319, 304

Component 1: $M^+$ 493, 436, 376, 366, 363, 338, 335, 320

This material was converted to its sulfate salt by dissolving in ethanol and adding a few drops of ethanol containing sulfuric acid. The resulting white solid was collected and dried to yield 22 mg. of Component 1, O-3-deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-D-streptamine as the di-base.heptasulfate.decahydrate, m.p. > 300°C.

Anal. Calcd. for $(C_{21}H_{43}N_5O_8)_2 \cdot 7H_2SO_4 \cdot 10H_2O$: C,27.22; H,6.53; N,7.55; S,12.09. Found: C,27.15; H,6.67; N,7.79; S,12.76.

Fractions 10–13 yielded a more polar ninhydrin component designated O-3-deoxy-4-C-methyl-3-methylamino-$\beta$-L-arabinopyranosyl-(1 → 6)-O-[2,6-diamino-6-C-methyl-2,3,4,6-tetradeoxy-$\alpha$-D-erythro-glucopyranosyl-(1 → 4)]-D-streptamine. Component 2, which displayed antibiotic activity.

Fractions 15–26 yielded a third more polar component displaying antibiotic activity. The mass spectrum of this component showed characteristic sugar peaks corresponding to gentamicin $C_{1a}$ at 129 (purpurosamine) and 160 (garosamine) and is designated 0-3-deoxy-4-C-methyl-3-methylamino-$\beta$-L-arabinopyranosyl-(1 → 6)-O-[2,6-diamino-2,3,4,6-tetradeoxy-$\alpha$-D-erythro-glucopyranosyl-(1 → 4)]-D-streptamine, Component 3.

Alternatively, the new Component 1 was isolated as follows: A mixture of crude antibiotic base obtained as above (0.9 g.) was dissolved in 7 ml. of water and the pH adjusted to 4.5 with 1N sulfuric acid. The solvent was passed over a strong anion exchange column (IRA 401) in the $OH^-$ form (bed measurement = 0.7 × 10 cm). The column was eluted with water and the eluate evaporated in vacuo at 35°C. The resulting residue was triturated with 50 ml. of the lower phase of a solvent composed of 17% aqueous ammonium hydroxide:isopropyl alcohol:chloroform (1:1:2). The solvent was decanted and concentrated under vacuum leaving an oily residue weighing 140 mg. The mass spectrum of this material corresponds to that from fractions 8 and 9 above, i.e., $M^+$ 493, 436, 376, 366, 363, 338, 335, 320.

The nuclear magnetic resonance spectrum for Component 1 was also consistent for the proposed structure corresponding to O-3-deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-D-streptamine and is summarized in Table II.

Table II

| $\delta$ | Integration | Assignment |
| --- | --- | --- |
| 5.87, 5.60 | 2 | anomeric OCHO's |
| 5.22 | 12 | exchangeable H |
| 3.09, 3.15 | 6 | $NCH_3 \times 2$ |
| 2.9–4.8 | 13 | —CHO × 6,—CHN × 5, —$CH_2O$ |
| 1.9–2.6 | 4 | —$CH_2CH_2$— |
| 1.72 | 6 | $CH_3C$—,$C\underline{H}_3CH$ |

Alternatively, a 4 g. sample of the crude antibiotic salt was dissolved in 50 ml. of water and passed over an anion exchange resin AG1X8 (resin bed 1 × 27 cm.). The antibiotic was eluted with water and all active fractions combined and evaporated under vacuum. Further desalting was carried out on the residue by extraction with methanolic sodium hydroxide. The liberated base was mixed with 7 g. of silica gel and charged on a 50 g. silica gel column. This column was developed with chloroform: methanol:concentrated(28%)ammonium hydroxide (3:4:2) and 25 ml. fractions collected. Early fractions yielded the new less polar Component 1 but admixed with several less polar impurities as evidenced by thin layer chromatography. These fractions were combined and the concentrate charged on a 50 g. silica gel column as above. This column was developed with chloroform:methanol:concentrated(28%)ammonium hydroxide (5:3:1) and 25 ml. fractions collected. Fractions 6–12 contained the desired component free of obvious impurities. On removal of solvent, the resulting oil was converted to the sulfate salt in ethanolic sulfuric acid as previously described yielding 0.124 g. of Component 1 as the dibase.heptasulfate.decahydrate, m.p. > 300°C. described above.

By culturing an appropriate aminocyclitol with mutant *Micromonospora purpurea* ATCC 31,119, in germination medium 2 and isolation of the products as described above in Example 1, the following compounds of formula I are similarly prepared:

EXAMPLE 2

O-3-Deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]epistreptamine (C.M. relative to gentamicin $C_1$: System 1=0.59, System 2=0.63);

O-3-deoxy-4-C-methyl-3-methylamino-$\beta$-L-arabinopyranosyl-(1 → 6)-O-[2,6-diamino-6-C-methyl-2,3,4,6-tetradeoxy-$\alpha$-D-erythro-glucopyranosyl-(1 → 4)]epistreptamine; and O-3-deoxy-4-C-methyl-3-methylamino-$\beta$-L-arabinopyranosyl-(1 → 6)-O-[2,6-diamino-2,3,4,6-tetradeoxy-$\alpha$-D-erythro-glucopyranosyl-(1 → 4)]epistreptamine obtained by use of epistreptamine in place of streptamine in the fermentaion procedure.

EXAMPLE 3

O-3-Deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-2,5-dideoxystreptamine (C.M. relative to gentamicin $C_1$: System 1=0.95, System 2=0.98);

O-3-deoxy-4-C-methyl-3-methylamino-$\beta$-L-arabinopyranosyl-(1 → 6)-O-[2,6-diamino-6-C-methyl-2,3,4,6-tetradeoxy-$\alpha$-D-erythro-glucopyranosyl-(1 → 4)]-2,5-dideoxystreptamine (C.M. relative to gentamicin $C_1$: System 1=0.66, System 2=0.73); and O-3-deoxy-4-C-methyl-3-methylamino-$\beta$-L-arabinopyranosyl-(1 → 6)-O-[2,6-diamino-2,3,4,6-tetradeoxy-$\alpha$-D-erythro-glucopyranosyl-(1 → 4)]2,5-dideoxystreptamine obtained by use of dideoxystreptamine in place of streptamine in the fermentation procedure.

The same O-3-deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-2,5-dideoxystreptamine; and O-3-deoxy-4-C-methyl-3-methylamino-$\beta$-L-arabinopyranosyl-(1 → 6)-O-[2,6-diamino-6-C-methyl-2,3,4,6-tetradeoxy-$\alpha$-D-erythro-glucopyranosyl-(1 → 4)]-2,5-dideoxystreptamine described above and having the same C.M. values as given above were obtained by use of 6,7-diazabicyclo[3.2.1]octane-2,4-diol (exo, exo) in place of streptamine in the fermentation procedure.

EXAMPLE 4

O-3-Deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-5-iodo-2,5-dideoxystreptamine;

O-3-deoxy-4-C-methyl-3-methylamino-$\beta$-L-arabinopyranosyl-(1 → 6)-O-[2,6-diamino-6-C-methyl-2,3,4,6-tetradeoxy-$\alpha$-D-erythro-glucopyranosyl-(1 → 4)]-5-iodo-2,5-dideoxystreptamine; and O-3-deoxy-4-C-methyl-3-methylamino-$\beta$-L-arabinopyranosyl-(1 → 6)-O-[2,6-diamino-2,3,4,6-tetradeoxy-$\alpha$-D-erythro-glucopyranosyl-(1 → 4)]-5-iodo-2,5-dideoxystreptamine obtained by use of 5-iodo-2,5-dideoxystreptamine in place of streptamine in the fermentation procedure.

EXAMPLE 5

O-3-Deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-5-fluoro-2,5-dideoxystreptamine;

O-3-deoxy-4-C-methyl-3-methylamino-$\beta$-L-arabinopyranosyl-(1 → 6)-O-[2,6-diamino-6-C-methyl-2,3,4,6-tetradeoxy-$\alpha$-D-erythro-glucopyranosyl-(1 → 4)]-5-fluoro-2,5-dideoxystreptamine; and O-3-deoxy-4-C-methyl-3-methylamino-$\beta$-L-arabinopyranosyl-(1 → 6)-O-[2,6-diamino-2,3,4,6-tetradeoxy-$\alpha$-D-erythro-glucopyranosyl-(1 → 4)]-5-fluoro-2,5-dideoxystreptamine obtained by use of 5-fluoro-2,5-dideoxystreptamine in place of streptamine in the fermentation procedure.

Synthesis of Amino-hydroxy-lower-alkanoyl Derivatives

EXAMPLE 6

A solution of 270 mg. (0.54 millimole) of O-3-deoxy-4-C-methyl-3-methylamino-$\beta$-L-arabinopyranosyl-(1 → 6)-O-[2-amino-6-methylamino-6-C-methyl-2,3,4,6-tetradeoxy-$\alpha$-D-erythro-glucopyranosyl-(1 → 4)]-D-streptamine, described above in Example 1 (Component 1), dissolved in 5 ml. of 50% aqueous tetrahydrofuran was cooled to 5°C. in an ice bath and treated with 208 mg. (0.59 millimole) of the N-hydroxysuccinimide ester of S-(−)-$\gamma$-(N-benzyloxycarbonyl-)amino-$\alpha$-hydroxybutyric acid (Konishi et al. U.S. Pat. No. 3,780,018), and the mixture was stirred at 5°C. for 20 hours. The mixture was then concentrated to 10 ml. in vacuo. n-Butanol (25 ml.) and water (10 ml.) were added, and the layers were separated. The aqueous layer was washed again with 10 ml. of n-butanol. The combined organic layers were evaporated leaving a residue of 513 mg. of crude product which was set aside.

The aqueous layer was evaporated to dryness to give 304 mg. of residue which was dissolved in 25 ml. of 50% aqueous tetrahydrofuran and treated with an additional 208 mg. of the N-hydroxysuccinimide ester of S-(−)-γ-(N-benzyloxycarbonyl)-amino-α-hydroxybutyric acid as before. Work up of the reaction mixture afforded an additional 435 mg. of crude product which was combined with the 513 mg. previously obtained and chromatographed on seven 40 × 20 cm. silica gel plates 1 mm. thick. The system was developed with chloroform:methanol:concentrated (28%)ammonium hydroxide (3:1:1) (lower phase). Seven passes in this solvent system were necessary, and after eluting the product band which was ultraviolet visible, 229.5 mg. of a crude mixture of the three monoacylated products was obtained.

The mixture of acylated products was put on three 40 × 20 cm. silica gel plates 1 mm. thick and the plates developed five times with chloroform:isopropanol:concentrated(28%) ammonium hydroxide (4:1:1) (lower phase), twice with chloroform:isopropanol:concentrated(28%)ammonium hydroxide (3:1:1) (lower phase) and nine times with chloroform:methanol:concentrated(28%) ammonium hydroxide (4:1:1) (lower phase). Three distinct bands visible under ultraviolet irradiation were obtained which were separately cut out and eluted from the silica gel with chloroform:methanol:concentrated(28%)ammonium hydroxide (1:1:1) (lower phase) affording three components: A,90.9 mg.; B,59.1 mg.; and C,48.5 mg., which are the S-(−)-γ-(N-benzyloxycarbonyl)-amino-α-hydroxybutyric acid amide derivatives at the 2'-, 1- and 3-positions, respectively, of O-3-deoxy-4-C-methyl-3-methyl-amino-β-L-arabinopyranosyl-(1 → 6)-O-[2-amino-6-methylamino-6-C-methyl-2,3,4,6-tetradeoxy-α-D-erythro-glucopyranosyl-(1 → 4)]-D-streptamine. The $R_f$ values for components A, B and C, when developed five times on silica gel with a chloroform:methanol:concentrated(28%)ammonium hydoxide (4:1:1) (lower phase) system, were:

A - 0.48
B - 0.62
C - 0.70

Component B (the 1-amide, 56.1 mg.) dissolved in 25 ml. of 50% aqueous ethanol and 20 mg. of 10% palladium-on-charcoal was shaken on a Parr shaker at 55 p.s.i. for 5½ hours after which time the catalyst was removed by filtration through filter aid. Evaporation of the solvent afforded 34.3 mg. of a white glass which was dissolved in 2.5 ml. of water and treated with 11.4 mg. of sulfuric acid in 0.1 ml. of water. Addition of 10 ml. of ethanol precipitated 1-[S-(−)-γ-amino-α-hydroxybutyryl]-O-3-deoxy-4-C-methyl-3-methylamino-β-L-arabinopyranosyl-(1 → 6)-O-[2-amino-6-methylamino-6-C-methyl-2,3,4,6-tetradeoxy-α-D-erythro-glucopyranosyl-(1 → 4)]-D-streptamine as the pentasulfate salt (32 mg.), m.p. 230°–235°C. (decomp.); tlc, $R_f$=0.18 (silica gel, chloroform:methanol:concentrated(28%)ammonium hydroxide:water, 1:4:2:1; $R_f$ gentamicin $C_1$ standard=0.73).

Anal. Calcd. for $C_{25}H_{50}O_{10}N_6 \cdot 5H_2SO_4$:C,27.67;H,5.57;N,7.75. Found: C,27.50;H,5.58;N,7.42.

Components A and C were treated in a similar fashion. A afforded 47 mg. of 2'-[S-(−)-γ-amino-α-hydroxybutyryl]-O-3-deoxy-4-C-methyl-3-methylamino-β-L-arabinopyranogyl-(1 → 6)-O-[2-amino-6-methylamino-6-C-methyl-2,3,4,6-tetradeoxy-α-D-erythro-glucopyranosyl-(1 → 4)]-D-streptamine as the bis-base.tetrasulfate.heptahydrate, m.p. 237°–241°C. (decomp.); tlc, $R_f$=0.33 [silica gel, chloroform:methanol:concentrated(28%)ammonium hydroxide:water, 1:4:2:1; $R_f$ gentamicin $C_1$ standard=0.73].

Anal. Calcd. for $(C_{25}H_{50}N_6O_{10})_2 \cdot 4H_2SO_4 \cdot 7H_2O$:C, 35.16;H,7.20;N,9.84. Found: C,35.38;H,7.08;N,9.49.

Component C afforded 26 mg. of 3-[S-(−)-γ-amino-α-hydroxybutyryl]-O-3-deoxy-4-C-methyl-3-methylamino-β-L-arabinopyranosyl-(1 → 6)-O-[2-amino-6-methylamino-6-C-methyl-2,3,4,6-tetradeoxy-α-D-erythro-glucopyranosyl-(1 → 4)]-D-streptamine as the bis-base.pentasulfate.trihydrate, m.p. 220–230°C. (decomp.); tlc. $R_f$=0.30 [silica gel, chloroform:methanol:concentrated(28%)ammonium hydroxide:water, 1:4:2:1; $R_f$ gentamicin $C_1$ standard=0.73].

Anal. Calcd. for $C_{25}H_{50}N_6O_{10})_2 \cdot 5H_2SO_4 \cdot 3H_2O$: C,34.64;H,6.74;N,9.67. Found: C,34.35;H,6.38;N,8.60.

Proceeding in a manner similar to that described in Example 6 using the respective antibiotics described in Examples 2, 3, 4 and 5 and either the N-hydroxysuccinimide ester of S-(−)-γ-(N-benzyloxycarbonyl)amino-α-hydroxybutyric acid or the pentafluorophenyl ester of N-(benzyloxycarbonyl)-(S)-isoserine [(S)-β-amino-α-hydroxypropionic acid[, described by Haskell et al., Carbohydrate Research, 28, 273–280 (1973), the following compounds of formula I are similarly prepared:

EXAMPLE 7

1-[(S)-β-Amino-α-hydroxypropionyl]-O-3-deoxy-4-C-methyl-3-methylamino-β-L-arabinopyranosyl-(1 → 6)-O-[2,6-diamino-6-C-methyl-2,3,4,6-tetradeoxy-α-D-erythro-glucopyranosyl-(1 → 4)]epistreptamine and 2'-[(S)-β-amino-α-hydroxypropionyl]-O-3-deoxy-4-C-methyl-3-methylamino-β-L-arabinopyranosyl-(1 → 6)-O-[2,6-diamino-6-C-methyl-2,3,4,6-tetradeoxy-α-erythro-glucopyranosyl-(1 → 4)]epistreptamine.

EXAMPLE 8

1-[S-(−)-γ-Amino-α-hydroxybutyryl]-O-3-deoxy-4-C-methyl-3-methylamino-β-L-arabinopyranosyl-(1 → 6)-O-[2,6-diamino-2,3,4,6-tetradeoxy-α-D-erythro-glucopyranosyl-(1 → 4)]-2,5-dideoxystreptamine and 2'-[S-(−)-γ-amino-α-hydroxybutyryl]-O-3-deoxy-4-C-methyl-3-methylamino-β-L-arabinopyranosyl-(1 → 6)-O-[2,6-diamino-2,3,4,6-tetradeoxy-α-D-erythro-glucopyranosyl-(1 → 4)]-2,5-dideoxystreptamine.

EXAMPLE 9

1-[(S)-β-Amino-α-hydroxypropionyl]-O-3-deoxy-4-C-methyl-3-methylamino-β-L-arabinopyranosyl-(1 → 6)-O-[2,6-diamino-2,3,4,6-tetradeoxy-α-D-erythro-glucopyranosyl(1 → 4)]-5-iodo-2,5-dideoxystreptamine and 2'-[(S)-β-amino-α-hydroxypropionyl]-O-3-deoxy-4-C-methyl-3-methylamino-β-L-arabinopyranosyl-(1 → 6)-O-[2,6-diamino-2,3,4,6-tetradeoxy-α-D-erythro-glucopyranosyl-(1 → 4)]-5-iodo-2,5-dideoxystreptamine.

EXAMPLE 10

1-[S-(−)-γ-Amino-α-hydroxybutyryl]-O-3-deoxy-4-C-methyl-3-methylamino-β-L-arabinopyranosyl-(1 → 6)-O-[2-amino-6-methylamino-6-C-methyl-2,3,4,6-tetradeoxy-α-D-erythro-glucopyranosyl-(1 → 4)]-5-fluoro-2,5-dideoxystreptamine and 2'-[S-(−)-γ-amino-α-hydroxybutyryl]-O-3-deoxy-4-

C-methyl-3-methylamino-β-L-arabinopyranosyl-(1 → 6)-O-[2-amino-6-methylamino-6-C-methyl-2,3,4,6-tetradeoxy-α-D-erythro-glucopyranosyl-(1 → 4)]-5-fluoro-2,5-dideoxystreptamine.

Antibacterial Test Results

The O-3-deoxy-4-C-methyl-3-methylamino-β-L-arabinopyranosyl-(1 → 6)-O-[2-amino-6-methylamino-6-C-methyl-2,3,4,6-tetradeoxy-α-D-erythro-glucopyranosyl-(1 → 4)]-D-streptamine described above in Example 1 and designated Component 1 was tested in comparison with gentamicin against a number of micro organisms according to the following procedure.

Stock solutions of each compound, containing 200 mcg./ml. base, were prepared in distilled water and filter sterilized. Cultures of the test organisms were grown for 24 hours at 37°C. in 10 ml. tubes of tryptose phosphate or Mueller-Hinton broth. Each culture was adjusted with broth to 0.1 optical density on a Spectronic 20 (approximately $1^8$ cells/ml.). The adjusted cultures were diluted 1:500 in broth for use as inoculum (final cell concentration approximately $2 \times 10^5$ cells/ml.). The test compounds were tested for antibacterial activity by a single-row tube dilution method. Master two-fold serial dilutions were made in broth from the stock drug solutions, and 0.2 ml. of each drug concentration was placed in seventeen $13 \times 100$ mm. tubes. All tubes were inoculated with 0.2 ml. of the appropriate diluted culture (final cell concentration per tube = $10^5$ cells/ml.) Minimum inhibitory concentrations (lowest drug concentration showing no visible growth) were read after 16 hours incubation at 37°C.

The results are given in Table III below. The compounds were considered inactive at inhibitory concentrations greater than 100 mcg./ml.

Table III*

| Organism | Minimal Inhibitory Conc. (mcg./ml.) | |
|---|---|---|
|  | Component 1 | Gentamicin |
| *Staphylococcus aureus* Smith | 0.78 | 0.195 |
| *Escherichia coli* Vogel | 3.13 | 3.13 |
| *Escherichia coli* W677/HJR66 | 50 | Inactive |
| *Escherichia coli* JR 35 | 3.13 | 6.25 |
| *Escherichia coli* JR 76.2 | 6.25 | 100 |

Table III*-continued

| Organism | Minimal Inhibitory Conc. (mcg./ml.) | |
|---|---|---|
|  | Component 1 | Gentamicin |
| *Escherichia coli* JR 89 | 50 | 50 |
| *Escherichia coli* K12 ML 1629 | 3.13 | 1.56 |
| *Enterobacter cloacae* A-20960 | 1.56 | 25 |
| *Klebsiella pneumoniae* 39645 | 1.56 | 0.78 |
| *Klebsiella pneumoniae* A-20636 | 3.13 | 50 |
| *Proteus mirabilis* MGH-1 | 6.25 | 1.56 |
| *Providencia* 164 | 100 | Inactive |
| *Providencia stuartii* A-20894 | 100 | 100 |
| *Pseudomonas aeruginosa* MGH-2 | 3.13 | 0.39 |
| *Pseudomonas aeruginosa* A-20717 | 2.5 | ≤12.5 |
| *Pseudomonas aeruginosa* A-20741 | Inactive | Inactive |
| *Pseudomonas aeruginosa* A-20897 | 12.5 | Inactive |

*Cultured in tryptose phosphate broth.

The same Component 1 described above in Example 1, O-3-deoxy-4-C-methyl-3-methylamino-β-L-arabinopyranosyl-(1 → 6)-O-[2-amino-6-methylamino-6-C-methyl-2,3,4,6-tetradeoxy-α-D-erythro-glucopyranosyl-(1 → 4)]-D-streptamine, was tested in comparison with gentamicin complex ($C_1$, $C_2$ and $C_{1a}$) and gentamicin $C_1$, and the 1-, 3- and 2'-[S-(−)-γ-amino-α-hydroxy-butyryl]amides of Component 1, described above in Example 6, and designated, respectively, Component 1 (1-HABA), Component 2 (3-HABA) and Component 1 (2'-HABA), were tested in comparison with the corresponding 1-, 3- and 2'-[S-(−)-γ-amino-α-hydroxybutyryl] amides of gentamicin $C_1$ (all described by Konishi et al. U.S. Pat. No. 3,780,018, patented Dec. 18, 1973) and designated, respectively, $C_1$ (1-HABA), $C_1$ (3-HABA) and $C_1$ (2'-HABA). These results are given in Table IV below where test organisms 1, 2, 3, 4, 5 and 6 identify *B. subtilis* ATCC 6633, *S. aureus* Smith, *E. coli* JR 76.2, *Ent. cloacae* A-20960, *K. pneumoniae* A20636 and *Ps. aeruginosa* A-20897, respectively.

Table IV*

| Compound | Test Organisms | | | | | |
|---|---|---|---|---|---|---|
|  | 1 | 2 | 3 | 4 | 5 | 5 |
| Gentamicin $C_1$, $C_2$, $C_{1a}$ | ≤0.024 | 0.39 | 50 | 12.5 | 25 | >100 |
| Gentamicin $C_1$ | 0.049 | 0.78 | 50 | 12.5 | 25 | >100 |
| Component 1 | 0.098 | 1.56 | 6.25 | 0.78 | 3.13 | 25 |
| $C_1$ (1-HABA) | 0.39 | 3.13 | 12.5 | 3.13 | 6.25 | >100 |
| Component 1 (1-HABA) | 0.78 | 6.25 | 12.5 | 6.25 | 12.5 | >100 |
| $C_1$ (3-HABA) | 3.13 | 25 | >100 | 100 | >100 | >100 |
| Component 1 (3-HABA) | 6.25 | 50 | 100 | 50 | 50 | >100 |
| $C_1$ (2'-HABA) | 6.25 | 50 | 100 | 25 | 50 | >100 |
| Component 1 (2'-HABA) | 1.56 | 25 | 50 | 25 | 50 | >100 |

*Cultured in Mueller-Hinton broth.

We claim:
1. A compound having the formula:

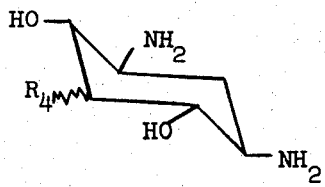

where $R_4$ is fluorine or iodine.

* * * * *